United States Patent
Kuhrts

(10) Patent No.: US 7,144,590 B2
(45) Date of Patent: Dec. 5, 2006

(54) BIOACTIVE COMPOSITIONS DERIVED FROM HUMULUS LUPULUS

(75) Inventor: Eric H. Kuhrts, Bodega, CA (US)

(73) Assignee: Lipoprotein Technologies, Inc.

( * ) Notice: Subject to any disclaimer, the term of this patent is extended or adjusted under 35 U.S.C. 154(b) by 441 days.

(21) Appl. No.: 10/340,183

(22) Filed: Jan. 9, 2003

(65) Prior Publication Data

US 2004/0137096 A1 Jul. 15, 2004

(51) Int. Cl.
*A01N 65/00* (2006.01)
(52) U.S. Cl. .................................... 424/725
(58) Field of Classification Search ................ 424/725
See application file for complete search history.

(56) References Cited

U.S. PATENT DOCUMENTS 4,640,841 A * 2/1987 Forster et al. ............. 426/425
5,955,086 A * 9/1999 DeLuca et al. ............ 424/745

FOREIGN PATENT DOCUMENTS

| AU | 8286745 | * | 2/1983 |
| CN | 1294183 | * | 5/2001 |
| JP | 02001017138 A | | 1/2001 |

OTHER PUBLICATIONS

Patrignani, Paola, "Biochemical and Pharmacological Characterization of the Cyclooxygenase Activity of Human Blood Prostaglandin Endoperoxide Synthases," Journal of Pharmacology and Experimental Therapeutics, 1994, pp. 1705-1711, vol. 271, No. 3.
Wolfe M. Michael, M.D. et al. "Gastrointestinal Toxicity of Nonsteroidal Antinflammatory Drugs", New England Journal of Medicine, vol. 340, No. 24, pp. 1888-1899, Jun. 17, 1999.
Brooks P. et al. "Interpreting the clinical significance of the differential inhibition of cyclooxygenase-1 and cyclooxygenase-2", British Society for Rheumatology, vol. 38, pp. 779-788, 1999.
Warner Timothy D. et al. "Nonsteroid drug selectivities for cyclo-oxygenase-1 rather than cyclo-oxygenase-2 are associated with human gastrointestinal toxicity: A full in vitro analysis", Proc. Natl. Acad. Sci. USA, vol. 96, pp. 7563-7568, Jun. 1999.
Yasukawa Ken et al. "Humulon, a Bitter in the Hop, Inhibits Tumor Promotion by 12-0-Tetradecanoylphorbol-13-Acetate in Two-Stage Carcinogenesis in Mouse Skin", Oncology, vol. 52, pp. 156-158, 1995.
Yamamoto Kei et al. "Suppression of cyclooxygenase-2 gene transcription by humulon of beer hop extract studied with reference to glucocorticoid", Federation of European Biochemical Societies, vol. 465, pp. 103-106, 2000.
Wallace J.L. et al., "NSAID-Induced Gastric Damage in the rat: Requirement for Inhibition of Both Cyclooxygenase-1 and Cyclooxygenase-2", Gastroenterology, vol. 119, pp. 706-714, 2000.

* cited by examiner

*Primary Examiner*—Michael Meller
(74) *Attorney, Agent, or Firm*—Thorpe North & Western

(57) ABSTRACT

Disclosed is a novel anti-inflammatory pharmaceutical composition that exhibits potent and selective inhibition of the cycloooxygenase-2 (COX-2) enzyme. The formulation consists of a hops extract that exhibits COX-2 selectivity as defined by dividing the IC50 COX-2/IC50COX-1 concentrations that are determined by testing with the William Harvey Whole Blood Assay (WHMA), and falls in the range of 0.011 to 0.2. Such compositions may also optionally contain high levels of alpha acids and low levels of beta acids, some flavonoid compounds, and virtually no essential oils. Such compositions are useful for treating conditions that manifest as inflammatory pain, or are impacted by the COX-2 enzyme. The recited compositions are particularly beneficial for treating osteoarthritis and rheumatoid arthritis, and can be used for chronic pain with reduced gastric side-effects.

36 Claims, No Drawings

BIOACTIVE COMPOSITIONS DERIVED FROM HUMULUS LUPULUS

BACKGROUND OF THE INVENTION

Research into the mechanism of inflammatory pain led to the discovery of the biochemical pathway associated with inflammation. One such example of chronic inflammatory pain is osteoarthritis. The elucidation of this pathway led to the association of the pro-inflammatory prostaglandins, produced by the cyclooxegenase enzyme, with pain and inflammation. The first generation of anti-inflammatory pain relievers, were classified as non-steroidal anti-inflammatory drugs or NSAIDs. Common NSAIDs such as aspirin, ibuprofen, naproxen, and indomethacin inhibit the cyclooxygenase enzyme, and thereby reduce inflammation by lowering the production of prostaglandin E-2. Many new NSAIDs were developed over the last 30 years, most of which are available by prescription only.

Until the emergence of the discovery of a second form of the cyclooxygenase enzyme, now called COX-2, there had been no distinction made between the various NSAIDs, in terms of the mechanism of action, and their effect, Only the magnitude of pain relief, or the potency for inhibiting the COX enzyme was considered important. However, side effects from the use of NSAIDs by patients who suffer from chronic inflammatory pain began to emerge. The principle side-effect was gastrointestinal toxicity, and it manifested in the form of gastric erosion, or erosion of the mucosal protective lining of the stomach. By the early 90s, as the incidence of osteoarthritis and rheumatoid arthritis increased, this side-effect became significant, leading to over 16,500 deaths per year in the United States alone. A review article by Wolf, M et al., *Gastrointestinal Toxicity of Nonsteroidal Antiinflammatory Drugs*, The New England Journal of Medicine, Vol. 340, No. 24, 1888–1899 (1999), is hereby incorporated by reference in its entirety. According to this article, 13 of every 1000 patients with rheumatoid arthritis who take NSAIDs for one year have a serious gastrointestinal complication. According to data from the National Center for Health Statistics and the Arthritis, Rheumatism, and Aging Medical Information System, yearly deaths from NSIAD toxicity (1997) in patients suffering from rheumatoid arthritis or osteoarthritis constitute the 15th leading cause of death in America. This figure is similar to mortality from AIDS (16,685) and only slightly less than deaths from Leukemia (20,197), but considerably greater than the number of deaths from multiple myeloma, asthma, cervical cancer, or Hodgkin's disease.

While most NSAIDs are more selective for the COX-1 form of the enzyme, they also inhibit the COX-2 form to varying degrees. Some NSAIDs, such as indomethacin, reduce both COX-1 and COX-2 to the same degree. Surprisingly, NSAIDs can also induce or up-regulate COX-2.

The potency of NSAIDs to cause gastric erosion and rapidly induce COX-2 can be illustrated by observing data from animal studies in which COX-2 was induced in the rat stomach within 1 hour of administration of aspirin or indomethacin. Both short term and long term administration of NSAIDs have produced gastric erosion as verified by endoscopy studies. Long term studies are defined as NSAID ingestion for at least 3 months, but usually are done over 3–6 months.

In the late 90s, a new class of prescription drugs emerged termed the COX-2 inhibitors. The first two compounds in this class approved by the U.S. FDA were celecoxib and rofecoxib. These drugs inhibited COX-2 with little or no effect on COX-1, and were sufficiently potent to produce equivalent pain relief to other NSIADs. While these compounds were no more effective than the NSAID pain relievers, chronic use resulted in virtually little gastrointestinal toxicity.

COX-2, or cyclooxygenase-2 inhibitors inhibit cyclooxygenase and reduce prostaglandins without producing the degree of gastric erosion associated with NSAID drugs such as aspirin. A COX-2 inhibitor selectively inhibits the COX-2 form of the enzyme more than the COX-1 form. To be classified as a good COX-2 inhibitor, a compound should inhibit COX-2 at least five times more than COX-1, or should have at least a 5:1 ratio of COX-2 to COX-1. Preferably, a COX-2 inhibitor should have an even greater selectivity than 5:1 for inhibiting COX-2, or from 5:1 to 100:1. A good COX-2 inhibitor would be capable of producing a concentration level in the blood that would reduce pain by 80 to 90% by inhibiting COX-2, with little or no effect on the COX-1 form of the enzyme. The terminology for quantifying the potency of a cyclooxygenase-2 inhibitor is the Inhibitory Concentration that produces a reduction of prostaglandin E-2 by 50%, termed the IC50. An even better index is the Inhibitory Concentration that produces an 80% reduction. This is called the IC80. For purposes of this application, the term IC80 shall refer to the concentration of the compound that produced an 80% reduction in the principle pro-inflammatory cytokine or prostaglandin, PGE-2. Conversely, the concentration of the compound capable of producing an 80% inhibition of the COX-2 enzyme could also be referred to as the IC80. Likewise, the IC50 shall mean the concentration of the compound that produces a 50% reduction in PGE-2, or a 50% reduction in the activity of the COX-2 enzyme.

In-vitro testing or screening of COX-2 inhibitors can be conducted by measuring the inhibition of prostaglandin E-2, a pro-inflammatory prostaglandin, in human whole blood. This results in the calculation of the IC50 values, or the amount or concentration of the compound needed to inhibit COX-2 by 50%, or the IC80 value, the concentration of the compound necessary to reduce prostaglandin E-2 by 80%. This testing model measures the production of prostaglandin E2 (PGE2) by the COX-2 enzyme related pathways, when stimulated by LPS or some other inducer of the COX-2 enzyme. COX-1 activity is also measured by measuring the production of thromboxane (TxB2). Such assays are now considered to represent a more complete in-vitro picture of COX-2/COX-1 selectivity and potency.

An international group of scientists published a consensus review related to COX-2 screening assays in: Brooks et al; *Interpreting the clinical significance of the differential inhibition of cyclooxygenase-1 and cyclooxygenase-2*, Rheumatology 1999; 38: 779–788. In this consensus paper, the committee stated that the Human Whole Blood Assay developed by Patrignani et al (J Pharmacol Exp Ther 1994; 271: 1705–12) was the best assay available for assessing inhibition of COX-1 and COX-2, or evaluating new COX inhibitors. More recently, the William Harvey Modified Human Whole Blood Assay was developed as an extension of the original whole blood assay, and most of the NSAID drugs, as well as the newer COX-2 inhibitors have been screened using this method.

To determine the COX-2/COX-1 inhibitory activity according to the invention the William Harvey Modified Human Whole Blood/Cell Assay (WHMA) is used, as set forth in T. D. Warner et al., *Nonsteroid drug selectivities for cyclo-oxygenase-1 rather than cyclo-oxygenase-2 are associated with human gastrointestinal toxicity: A full in vitro* analysis, Proc. Natl. Sci. USA 96:7563–68 (1999), hereby incorporated by reference in its entirety. The results from this assay are used to calculate the IC50 and IC80-WHMA COX-2/COX-1 ratio, which is simply the numerical ratio of the COX-2 IC50 concentration divided by the COX-1 IC50 concentration, obtained using the WHMA. In addition, the potency of the compound for reducing or inhibiting COX-2 is thereby determined. This is done by measuring the inhibition of the two isoforms of the enzyme at different concentrations of the inhibitor, starting at very low concentrations, and increasing in a log fashion until at least an 80% inhibition is produced. This results in a log graph of the concentration versus inhibition curve, or a dose response curve.

Numerous studies have shown that the relative incidence of GI side effects from NSAIDs can be correlated to the relative COX-2 specificity of these anti-inflammatory agents. The higher the specificity for COX-2 over COX-1, the lower the incidence of GI upsets. Accordingly, cyclooxygenase inhibiting agents with increased COX-2 specificity may provide improved anti-inflammatory compositions having less incidences of gastrointestinal distress or side effects. It is becoming increasingly apparent that the gastric damage that can be caused by NSAIDs is not just related to their effect on COX-1. Dual suppression of COX-1 and COX-2 seems to be necessary for damage to occur (Wallace, J L et al., *NSAID-Induced Gastric Damage in the rat: Requirement for Inhibition of Both Cyclooxygenase-1 and Cyclooxygenase-2*. Gastroenterology, 2000; 119:706–14). Furthermore, selective inhibition of COX-1, which greatly reduced prostaglandin synthesis, did not produce gastric damage in the same study. On the other hand, selective inhibition of COX-2 did not appear to have any effect on gastric prostaglandin synthesis, and did not produce gastric damage.

Interestingly, when both COX-1 and COX-2 were inhibited, gastric damage was consistently observed. This, and other research, is providing a clearer picture of the relationship between COX-1, COX-2, and gastric erosion. It now appears that combined inhibition of COX-1 and COX-2 contribute to the side-effects, but more highly selective inhibition of either COX-1 or COX-2 alone, is not responsible.

However, too much selectivity for COX-2 over COX-1 may not be desirable for other reasons. Certain side-effects may result from COX inhibitors that are extremely selective for COX-2. For example, the cardiovascular benefit of aspirin, a predominantly COX-1 non-steroidal anti-inflammatory drug (NSAID), is thought to be due to its activity as an anti-platelet aggregating drug. COX-2 inhibition does not result in anti-platelet aggregation. Current pharmaceutical COX-2 inhibitors, such as celecoxib or rofecoxib, are highly specific COX-2 inhibitors, and would not be expected to have any COX-1 inhibitory activity at the doses used to reduce pain and inhibit COX-2 activity. Thus, the cardiac-related side effects that have been noted with the use of some COX-2 specific inhibitors may be related to the lack of any COX-1 inhibition while significantly inhibiting COX-2.

Furthermore, an additional problem associated with highly specific COX-2 inhibitors is the increase in gastric erosion produced by concurrent administration with other non-steroidal anti-inflammatory drugs (NSAIDS). For example, if a patient is taking a highly selective COX-2 inhibitor and also takes aspirin for cardiovascular benefit, the aspirin will cause even worse damage to the gastric mucosa. The reason for this is that some of the prostaglandins that are inhibited by cyclooxygenase inhibitors, such as prostaglandin E-2 (PGE2), are protective of the gastric mucosa, and actually contribute to healing of ulceration. Low dose aspirin produces small erosions in the stomach, and at the site of these ulcerations, the COX-2 enzyme becomes up-regulated. When COX-2 is blocked by selective COX-2 inhibitors, the protection afforded by the beneficial prostaglandins is eliminated. The result is that the ulcerative damage is made even worse. Concomitant administration of selective COX-2 inhibitors with aspirin is therefore contraindicated. This phenomenon is an indication of the problems associated with the dual inhibition of both COX-1 and COX-2. Thus gastric erosion will be worse with a single compound that exhibits significant inhibition of both COX-1 and COX-2, or by combining a COX-2 selective compound with a non-selective COX inhibitor that also inhibits COX-1 to a large degree. The key to overall risk reward benefits would be to have just the right amount of COX-1 inhibition along with predominantly COX-2 inhibition. The ratio of IC50COX-2/IC50COX-1 would be from about 1:5 to 1:100 or numerically from 0.20 to 0.010. Preferably, the ratio of IC50COX-2/IC50COX-1 would be at least 20:1 or numerically 0.05. For example, a compound that is tested using the WHMA protocol might have an IC50 for COX-2 of 1 μg/ml and an IC50 for COX-1 of 20 μg/ml, therefor, the IC50COX-2/IC50COX-1 ratio would be 1:20 or 0.05.

In summary, highly selective single entity COX-2 inhibitors such as rofecoxib and celecoxib, while important new drugs for the treatment of pain associated with osteoarthritis and other maladies, have some serious potential side-effects. These side effects can be divided into two major groups; 1) cardiovascular, and 2) worsening of gastric erosion when taken with aspirin or other NSAIDS. Both of these side effects may be related to an unbalanced total inhibition of the COX enzyme, and therefor, virtually complete blocking of prostaglandin production. Because prostaglandins have both positive and negative functions in the body, their total inhibition is a double-edged sword. Furthermore, there is a significant overlap in the patient populations that take both aspirin for cardiovascular benefit, and a selective COX-2 inhibitor for pain. Most of these subjects primarily consist of the elderly population. There is a significant need for anti-inflammatory pain relief without the negative side effects of the NSAIDs or the selective COX-2 inhibitors. Such a composition would provide pain relief while also inhibiting platelet aggregation, and providing protection for the gastric mucosa through some gastroprotective or cytoprotective mechanism. These second generation COX-2 inhibitors would be selective enough to inhibit COX-2 over COX-1, but not so selective that they would result in the additional side effects mentioned above. These compounds may exhibit protective activity by virtue of the existence of some other beneficial properties.

In the search for new anti-inflammatory compounds, many potential candidates have come from the plant kingdom. These botanicals are usually extracted and tested in-vitro for COX inhibition using various cell lines and methods. Usually these methods involve screening the compounds for COX-2 and COX-1 inhibition by measuring the inhibition of prostaglandin E-2 for COX-2 inhibition, and TxB2 for COX-1 inhibition. Selectivity can then be determined by calculating the COX-2/COX-1 ratio, or conversely, the COX-1/COX-2 ratio.

It would be desirable to find compounds that exhibit good selective COX-2 inhibition, but with the least amount of cardiovascular or gastrointestinal side-effects. Such compounds would result in a broader spectrum of therapeutic benefit, and be tunable over a wide range of COX-2/COX-1 ratios, providing effective pain relief with less side-effects.

Such compounds could provide some minimal amount of COX-1 inhibition for cardiovascular benefit, without significant gastric erosion, while providing significant COX-2 inhibition for pain.

What are needed are compositions and methods that address the problems noted above.

DETAILED DESCRIPTION OF THE INVENTION

The present invention provides a composition that exhibits a selective inhibition of the COX-2 isoform of the cyclooxygenase enzyme while having at least a minimal effect on the COX-1 isoform. Minimal effect, for purposes of definition, shall mean at least 1% COX-1 inhibition activity. For example, 1% inhibition of COX-1 would correspond to a ratio of IC50COX-2/IC50COX-1 of 1:100 or 0.010, in other words, it would take 100 times more of the compound to inhibit COX-1 by 50% than the amount to inhibit COX-2.

As used in this application, the term IC50 or IC80 shall mean the concentration of the compound or formulation that produces a 50% or 80% inhibition of COX-1 or COX-2 in the William Harvey Modified Human Whole Blood/Cell Assay (WHMA).

As used in this application, WHMA shall be the abbreviation for the William Harvey Whole Blood Assay.

As used herein, the concentration of the COX inhibitor shall be designated as either micrograms per milliliter (abbreviated as μ/ml) or micro molar (abbreviated as μM).

As used herein, the COX ratios are calculated as the IC50COX-2/IC50COX-1, or IC80COX-2/IC80COX-1, but COX-2 will always be divided by COX-1.

As used herein, an oral dosage form shall mean a pharmaceutical formulation designed to be administered orally, consisting of various pharmaceutical carriers and excipients, and can be in tablet, capsule, buccal, sublingual, or suppository forms. Said oral dosage form will be absorbed in the human or animal oral cavity, gastrointestinal tract or via suppository.

The oral dosage form described herein may also be formulated in a sustained-release form, employing various polymers, fibers, resins, waxes, oils, or other pharmaceutical excipients used by those skilled in the art of medicinal chemistry to produce a prolonged release of the active constituents form the gastrointestinal tract. Such sustained-release dosage formulations are designed to provide for a longer residence time of the compound in the blood stream, thereby increasing the length of pain relief.

One such candidate is a special extract of Humulus lupulus L., or the plant commonly known as hops. Hops is derived from the cone flowers of the hops plant, and has been used in the production of beer for hundreds of years. Hops may exhibit some metabolic and endocrine effects. There are at least six flavonoids that can be isolated from hops, and some of these flavonoids have antiproliferative, estrogenic, and cytotoxic effects. The phytoestrogens in hops have also been shown to inhibit growth of human breast cancer cells. The unique flavonoid compounds isolated from hops (prenylated flavanoids) therefore may have potential as cancer chemopreventative agents by effecting the metabolism of carcinogens. The flavones contained in hops include xanthohumol, isoxanthohumol, desmethylxanthohumol, 8-prenylnaringenin, 6-prenylnaringenin, and various other flavonoids. Hops also exhibits antimicrobial and anti-fungal properties.

The primary constituents in hops consist of alpha acids and beta acids. The alpha acids have been identified as humulone, cohumulone, adhumulone, and dihydrohumulone. These alpha acids also exist as dihydro-alpha acids and as various isomers. The iso-alpha acids are iso-humulone, iso-cohumulone, iso-adhumulone, trans-iso-humulone, cis-iso-humulone, trans-iso-cohumulone, cis-iso-cohumulone, cis-iso-adhumulone, trans-iso-adhumulone, dihydro-iso-humulone, and dihydro-iso-adhumulone. The beta acids are lupulone, colupulone, adlupulone, prelupulone, and postlupulone. There are no isomers of the beta acids. Hops also contains various essential oils such as myrcene, caryophyllene, humulene, undecane-2-on, and 2-methyl-but-3-en-ol. These oils can be classified primarily as terpenes and sesqueterpenes. At least 50% of the essential oils consist of the terpene, myrcene.

Topical application of humulone, one of the alpha acids isolated from hops, inhibited arachidonic acid-induced inflammatory ear edema in mice (Yasukawa, K et al, Oncology 1995, March; 52 (2): 156–158), and also inhibited skin tumor formation following initiation with a chemical challenge. Pure humulon, has also been shown to suppress cyclooxygenase-2 induction at the level of gene transcription (Yamamoto K, et al, FEBS Lett 2000 Jan. 14, 465(2–3: 103–106). In this same study, humulone inhibited the catalytic activity of COX-2 in osteoblast (bone) MC3T3-E1 cells with an IC50 of 1.6 μM. Furthermore, humulone suppressed the TNF-alpha-dependent cyclooxygenase-2 induction in the same cell line. The direct inhibition of the COX-2 enzyme by humulone required a greater concentration than the concentration necessary to inhibit the gene transcription, or the suppression of COX-2 expression. Humulone appeared to be more effective at a lower concentration in preventing the transcription or activation of COX-2 by suppressing the gene transcription, than by direct inhibition of the COX-2 enzymes catalytic activity. The IC50 for suppression of COX-2 transcription was 30 ηM (10-9) whereas the IC50 for direct inhibition of catalytic activity was 1.6 μM (10-6), or two orders of magnitude lower. Only pure humulone was used in this study.

Special extracts of hops cone flowers can preferably be prepared employing supercritical carbon dioxide. Supercritical $CO_2$ extraction can result in extracts of hops that contain a very high percentage of alpha acids, very little beta acids, and essentially no essential oils. This invention, however, is not limited to the extraction technique. Preferred amounts of alpha acids in the instant invention can be from 75 wt % to 99.5 wt %. The alpha acids may be humulone, cohumulone, adhumulone, dihydrohumulone, or tetra-hydro-alpha acids such as tetra-hydrohumulone. The beta acids can be from 1 wt % to 10 wt %, preferably around 3–5%, or even less. Optionally, the composition may be substantially void of essential oils such as myrcene or other terpenes or sesqueterpenes. The composition may also contain iso-alpha acids to varying degrees. Usually the level of iso-alpha acids will be from 0.5 to 10%. The iso-alpha acids may be iso-humulone, iso-cohumulone, iso-adhumulone, di-hydro-iso-humulone, di-hydro-iso-adhumulone or combinations thereof The iso-alpha acids may be useful for tuning the selectivity for COX-2 in the formulation, by boosting the COX-1 component, and changing the COX-2/COX-1 ratio to be less selective for COX-2. The reason for these type of formulas may be to address cardiovascular issues by contributing some anti-platelet aggregation activity from the COX-1 inhibition via thromboxane.

The IC50 ratio of COX-2 to COX-1 or the IC50COX-2/IC50COX-1 can be in the range of 0.011 to 0.20, or from 1:90 to 1:5. The percentage of alpha acids can be from 60% to 99.5%, but is not limited to this range if the IC50COX-2/IC50COX-1 ratios fall within the specified ranges of 0.011 to 0.20. As mentioned, the iso-alpha acids may be from 0.5 wt % to 10 wt %. The beta acids range can be from 0.5 wt % to 10 wt %. Various polyphenols or flavonoids may be present such as xanthohumol, isoxanthohumol, 8-prenylnaringenin, 6-prenylnaringenin in varying amounts.

The compositions in this invention are not limited to the amount of alpha acids and beta acids, or the method of processing or extraction. For example, a hops extract that exhibits a WHMA IC50COX-2 over IC50COX-1 ratio of 0.013 (1:75) would be part of this invention regardless of the method of processing or the amount of alpha acids, beta acids, or essential oils. Powders of hops can be made which exhibit IC50COX-2/COX-1 ratios of 1:20 or 0.05, which provide good pain relief from chronic osteoarthritis or rheumatoid arthritis. Such compositions can also be useful for treating dysmenorrhea or menstrual pain, psoriasis, and other diseases impacted by COX-2.

In an aspect, the invention relates to a pharmaceutical composition comprising a therapeutic quantity of a COX-2 inhibitor having an IC50-WHMA COX-2/COX-1 ratio ranging from about 0.01 1 to about 0.20. An additional aspect of the invention, would be less gastrointestinal and cardiovascular side effects. Still further, an additional aspect is the treatment of a disease impacted by the COX-2 enzyme, especially inflammation, or a disease that manifests in the up-regulation or induction of COX-2. Some examples of such diseases include, but are not limited to; osteoarthritis, rheumatoid arthritis, dysmenorrea, and psoriasis. The compositions described herein may be used to treat any type of inflammation or pain associated with inflammation.

Compositions are also described that consist primarily of the alpha acids in hops, with little or no beta acids, and little or no essential oils. Furthermore, compositions that contain the various iso-alpha acids such as iso-humulone, iso-cohumulone, iso-adhumulone, trans-iso-humulone, cis-iso-humulone, trans-iso-cohumulone, cis-iso-cohumulone, cis-iso-adhumulone, trans-iso-adhumulone, dihydro-iso-humulone, and combinations thereof, may also be included.

EXAMPLES

In-vitro testing or screening of the recited COX-2 inhibitors can be conducted by measuring the inhibition of prostaglandin E-2, a pro-inflammatory prostaglandin. This results in the calculation of the IC50 and/or IC80 values, or the amount or concentration of the compound needed to inhibit COX-2 by 50% and/or 80%. This model measures the production of prostaglandin E2 (PGE2) by the COX-2 enzyme related pathways, when stimulated by LPS in an in-vitro cell line model. However, the human whole blood assay has been deemed the method of choice by a panel of experts for assessing and screening COX inhibitors (Brooks, P et al, *Interpreting the clinical significance of the differential inhibition of cyclooxygenase-1 and cyclooxygenase-2*, Rheumatology; 1999; 38: 779–788). Such assays are now considered to represent a more complete in-vitro picture of COX-2/COX-1 selectivity and potency. A modified version of the human whole blood assay called the William Harvey Modified Human Whole Blood Assay has been selected as one of the best models for testing the compositions described herein. To determine the COX-2/COX-1 inhibitory activity according to the invention, the William Harvey Modified Human Whole Blood/Cell Assay (WHMA) is used, as set forth in T. D. Warner et al., *Nonsteroid drug selectivities for cyclo-oxygenase-1 rather than cyclo-oxygenase-2 are associated with human gastrointestinal toxicity: A full in vitro analysis*, Proc. Natl. Sci. USA 96:7563–68. (1999). The results from this assay are used to calculate the IC50-WHMA COX-2/COX-1 ratio, which is simply the numerical ratio of the COX-2 IC50 divided by the COX-1 IC50 ratio, obtained using the WHMA.

Human whole blood (8 concentrations, n=4) is collected by venapuncture into heparin. For determining COX-1, incubation of test compound(s) was carried out for 1 hour, with addition of stimulus (A23187) for 30 minutes. For COX-2 incubation of test compounds in A549 cells in human whole blood was carried out for 1 hour, addition of stimulus (A23187) for 30 minutes. Following this, TxB2 is measured by RIA as an index of COX-1 activity, and PGE2 is measured by RIA as an index of COX-2 activity. The results are expressed as % control, and the COX-2/COX-1 ratio is calculated.

Example 1

COX-2 Inhibition Activity of Hops

A supercritical carbon dioxide extract of hops was produced that yielded 91% alpha acids, of which the principle alpha acid was humulone as verified by HPLC. The amount of beta acids in this extract was verified to be 3.2% and the amount of iso-alpha acids was about 3%. This extract was virtually devoid of the essential oils normally found in a typical hops powder or extract.

Hops extract constituents as identified by HPLC are as follows:

| | |
|---|---|
| Alpha acids | 88% |
| Beta acids | 3.2% |
| Iso-alpha acids | 3% |
| Total alpha acids | 91% |
| | (alpha and iso-alpha) |

This extract was dissolved in DMSO and tested according to the protocol described above.

The effects of test agents on COX-1 and COX-2 activity are detailed in Tables 1–3. Results in Tables 1–3 are expressed as % control and shown as mean ±s.e.m. (n=4) from which $IC_{50}$ values were calculated (Table 3).

TABLE 1

COX-1 activity in human whole blood (TxB$_2$, % control)

| | Concentration (log M) | | | | | | | |
|---|---|---|---|---|---|---|---|---|
| | −10 | −9 | −8 | −7 | −6 | −5 | −4 | −3 |
| Hops extract | 100 ± 6 | 103 ± 6 | 100 ± 5 | 94 ± 4 | 91 ± 5 | 80 ± 10 | 60 ± 15 | 18 ± 2 |

TABLE 2

COX-2 activity in A549 cells in human whole blood (PGE$_2$, % control)

| | Concentration (log M) | | | | | | | |
|---|---|---|---|---|---|---|---|---|
| | −10 | −9 | −8 | −7 | −6 | −5 | −4 | −3 |
| Hops extract | 97 ± 6 | 95 ± 6 | 87 ± 8 | 61 ± 8 | 54 ± 10 | 42 ± 10 | 16 ± 3 | 6 ± 2 |
| Ibuprofen | | 85 ± 16 | 82 ± 10 | 80 ± 9 | 80 ± 5 | 60 ± 4 | 20 ± 5 | 4 |

As can be seen from tables 1 and 2, a rather large amount of the hops extract is necessary to reduce COX-1 by 50% (the IC50 is 10-3 to 10-4), whereas, for COX-2, the concentration needed for 50% reduction is 10-6 (IC50 was 1.4×10-6 μM). It takes about 100 times as much of this 91% alpha acid hops extract to reduce COX-1 by 50% as the concentration needed to reduce COX-2 activity by 50%. Ibuprofen is included for comparison. The hops extract was more potent and selective than ibuprofen for inhibition of COX-2.

TABLE 3

Potencies of test agents on human COX-1 and COX-2 (WHMA)

| | IC$_{50}$ (μM) | | IC$_{50}$ ratio |
|---|---|---|---|
| | COX-1 | COX-2 | (COX-2/1) |
| Aspirin | 1.7 | 7.5 | 4.4 |
| Ibuprofen | 7.6 | 20 | 2.6 |
| Naproxen | 9.3 | 35 | 3.8 |
| Hops extract | 110 | 1.4 | 0.0127 |
| Celexocib | 2.2 | 0.34 | 0.3 |
| Rofecoxib | 63 | 0.31 | 0.0049 |
| Indomethacin | 0.0031 | 0.021 | 7 |

Table 3 is a comparison of the 91% alpha acid containing hops extract that was derived by supercritical carbon dioxide, with other known COX inhibitors, including the prescription COX-2 selective inhibitors rofecoxib and celexocib, as well as the non selective COX inhibitors aspirin, ibuprofen, naproxen and indomethacin. As can be seen from the above data, hops extract is a selective and potent COX-2 inhibitor when tested according to the WHMA protocol. The IC50 COX-2 concentration of this hops extract was about 1.4 μM, a concentration that would be within a range of pharmacological action of most non-steriodal anti-inflammatory drugs, whereas the IC50 COX-1 concentration was about 110 μM. The ratio was therefor 0.0127 or 1:90.

TABLE 4

Potencies of test agents on human COX-1 and A549 COX-2 (WHMA)

| | IC$_{50}$ (μM) | | IC$_{80}$ (μM) | | ratios (COX-2/1) | |
|---|---|---|---|---|---|---|
| | COX-1 | COX-2 | COX-1 | COX-2 | IC$_{50}$ | IC$_{80}$ |
| Hops extract | 110 | 1.4 | >1000 | 85 | 0.01 | <0.09 |
| indomethacin | 0.0069 | 0.055 | 0.027 | 0.21 | 8 | 8 |

Table 4 includes the IC80 data for the special hops extract compare to indomethacin, a potent non-selective NSAID that lowers COX-1 and COX-2 at a very low concentration. As can be seen from table 4 above, the IC80 for COX-2 was about 85 μM, and the IC80 COX-2/1 ratio was about 0.09 μM, which is a ratio of about 1:11. While not as potent as indomethacin, the selectivity for COX-2 is much greater.

While the resin used in the above experiment resulted in significant inhibition of the COX-2 enzyme with very little effect on the COX-1 form, such a resin is difficult to use in a pharmaceutical dosage form without converting to a powder. When converted to a powder, various excipients must be used as carriers which tend to dilute the potency of the resin, thereby reducing the IC50 or IC80 by about 50%, and also enabling various mixtures of alpha acids and iso-alpha acids to be employed.

Example 2

COX-2 Inhibition of a Hops Resin Converted to Powder

A hops resin is converted to powder using maltodextrin and calcium silicate in a jacketed high intensity mixer. The resulting powder was analyzed by HPLC and found to yield the following principle constituents:

| Alpha acids | 20% | Iso-alpha acids | 9.4% | Beta acids | 8% |
|---|---|---|---|---|---|

This powder was tested for COX-2 and COX-1 inhibition in a cell line in whole blood by inducing COX-2 with LPS (lipopolysaccharide) and measuring PGE-2 for COX-2 activity. COX-1 activity was assessed by measuring TxB2 (thromboxane B2). IC50 results for COX-2 and COX-1 were;

| IC50 COX-2 | IC50 COX-1 | IC50COX-2/IC50COX-1 |
|---|---|---|
| 1 μg/ml | 30 μg/ml | 0.033 (1:30) |

Example 3

This example is to demonstrate the reduction in gastric erosion of a hops formulation versus a traditional non-selective COX inhibitor NSAID such as aspirin. An oral formulation of a tablet containing 750 mg. of a hops extract powder consisting of 30% alpha acids (225 mg. alpha acids) is administered to 40 subjects in a single blind, parallel-group, multiple dose study. The patients are randomly assigned to treatment with either the hops alone or 1,000 mg. aspirin per day for 4 days. Assessments are made based on endoscopic evaluations of gastroduodenal irritancy performed 4 hours after the first dose and 3 hours after the final administration on the fourth study day. To assure that all study subjects had normal healthy gastroduodenal mucosa at baseline, an endoscopic evaluation is also performed before subjects are randomized.

Endoscopy is used to assess the extent and severity of gastric and duodenal damage. During an endoscopic examination of the stomach and duodenum, the number and location of submucosal hemorrhages, erosions, and ulcerations, are determined by the endoscopist. Based on the findings, the hemorrhagic damage is graded on a scale of 0–4 and the erosive damage is graded on a separate 0–4 scale. The stomach and duodenum are graded separately. Under the test conditions described above, endoscopic evaluation is expected to reveal virtually no gastric erosion form the hops formulation, while the aspirin formulation exhibited significant gastric submucosal hemorrhages and overall gastric erosions. The difference between the two groups is expected to be statistically significant. The reduction in gastric erosion of the hops formulation in comparison to aspirin is believed to be related to its selectivity for COX-2 over COX-1.

While the present invention is described above in connection with the preferred or illustrative embodiments, those embodiments are not intended to be exhaustive or limiting of the invention, but rather, the invention is intended to cover any alternatives, modifications, or equivalents that may be included within its scope as defined by the appended claims.

What is claimed is:

1. An anti-inflammatory composition, comprising a hops extract including a pharmaceutically effective amount of from 75 wt % to 99.5 wt % of alpha acid and from 0.5 wt % to 10 wt % of beta acid.

2. The composition of claim 1, wherein the alpha acid and beta acid are derived from hops cone flowers.

3. The composition of claim 1, wherein the alpha acid is selected from the group consisting of humulone, cohumulone, adhumulone, dihydrohumulone, dihydroadhumulone, and mixtures thereof.

4. The composition of claim 1, further comprising an iso-alpha acid selected from the group consisting of iso-humulone, iso-cohumulone, iso-adhumulone, dihydro-iso-humulone, dihydro-iso-adhumulone, and combinations thereof.

5. The composition of claim 4, wherein the iso-alpha acid comprises a member selected from the group consisting of trans-iso-humulone, cis-iso-humulone, trans-iso-cohumulone, cis-iso-cohumulone, cis-iso-adhumulone, trans-iso-adhumulone, and combinations thereof.

6. The composition of claim 1, wherein the beta acid is present at from 1 wt % to 10 wt %.

7. The composition of claim 1, wherein the hops extract is substantially void of essential oils.

8. The composition of claim 1, wherein the hops extract is formulated to treat inflammatory pain by oral delivery with reduced gastric side effects.

9. The composition of claim 1, further comprising a flavonoid or polyphenolic compound.

10. The composition of claim 9, wherein the flavonoid or polyphenolic compound is xanthohumol.

11. The composition of claim 9, wherein the flavonoid or polyphenolic compound is selected from the group consisting of isoxanthohumol, 8-prenylnaringenin, 6-prenylnaringenin, and combinations thereof.

12. The composition of claim 1, wherein the hops extract comprises greater than 80 wt % alpha acid and not more than 10 wt % iso-alpha acid.

13. The composition of claim 4, said composition being void of myrcene, beta-caryophyleen, undecane-2-on, and 2-methyl-but-3-en-ol.

14. The composition of claim 1, further comprising a pharmaceutical carrier, and wherein the dosage form is for alimentary delivery in the form of a tablet, capsule, or suppository.

15. The composition of claim 14 in a sustained-release formulation.

16. The composition of claim 1, wherein the hops extract has an WHMA IC50 COX-2/IC50COX-1 ratio of from about 0.011 to 0.20.

17. The composition of claim 16, wherein the hops extract has an WHMA IC50 COX-2/IC50COX-1 ratio of about 0.20.

18. The composition of claim 16, wherein the hops extract has an WHMA IC50 COX-2/IC50COX-1 ratio of about 0.011.

19. The composition of claim 16, wherein the hops extract has an WHMA IC50 COX-2/JC50COX-1 ratio from about 0.02 to 0.05.

20. An anti-inflammatory composition, comprising a hops extract having an WHMA IC50 COX-2/IC50COX-1 ratio of from about 0.011 to 0.20 and wherein said hops extract comprises 75 wt % to 99.5 wt. % of alpha acid and 0.5 wt % to 10 wt % of beta acid.

21. The composition of claim 20, wherein the alpha acid and beta acid are derived from hops cone flowers.

22. The composition of claim 20, wherein the alpha acid is selected from the group consisting of humulone, cohumulone, adhumulone, dihydrohumulone, tetra hydro-alpha-acids, and mixtures thereof.

23. The composition of claim 20, further comprising an iso-alpha acid selected from the group consisting of iso-humulone, iso-cohumulone, iso-adhumulone, dihydro-iso-humulone and combinations thereof.

24. The composition of claim 23, wherein the iso-alpha acid comprises a member selected from the group consisting of trans-iso-humulone, cis-iso-humulone, trans-iso-cohumulone, cis-iso-cohumulone, cis-iso-adhumulone, trans-iso-adhumulone, and combinations thereof.

25. The composition of claim 20, wherein the hops extract is substantially void of essential oils.

26. The composition of claim 20, wherein the hops extract is formulated to treat inflammatory pain by oral delivery with reduced gastric side effects.

27. The composition of claim 20, further comprising a flavonoid or polyphenolic compound.

28. The composition of claim 27, wherein the flavonoid or polyphenolic compound is xanthohumol.

29. The composition of claim 27, wherein the flavonoid or polyphenolic compound is selected from the group consisting of isoxanthohumol, 8-prenylnaringenin, 6-prenylnaringenin, and combinations thereof.

30. The composition of claim 20, wherein the hops extract comprises greater than 80 wt % alpha acid and not more than 10 wt % iso-alpha acid.

31. The composition of claim 23, said composition being void of myrcene, beta-caryophyleen, undecane-2-on, and 2-methyl-but-3-en-ol.

32. The composition of claim 20, comprising a pharmaceutical carrier, and wherein the dosage form is for alimentary delivery in the form of a tablet, capsule, or suppository.

33. The composition of claim 32 in a sustained-release formulation.

34. The composition of claim 20, wherein the hops extract has an WHMA IC50 COX-2/IC50COX-1 ratio of about 0.02.

35. The composition of claim 20, wherein the hops extract has an WHMA IC50 COX-2/IC50COX-1 ratio of about 0.011.

36. The composition of claim 20, wherein the hops extract has an WHMA IC50 COX-2/IC50COX-1 ratio range from about 0.02 to 0.05.

* * * * *